United States Patent [19]

Kagayama et al.

[11] Patent Number: 5,178,834
[45] Date of Patent: Jan. 12, 1993

[54] AUTOMATIC IMMUNOASSAY ANALYZER

[75] Inventors: Toshi Kagayama, Yokohama; Shuji Iwasaki, Fujisawa, both of Japan

[73] Assignee: Tosoh Corporation, Yamaguchi, Japan

[21] Appl. No.: 892,486

[22] Filed: Jun. 3, 1992

Related U.S. Application Data

[63] Continuation of Ser. No. 554,507, Jul. 19, 1990, abandoned.

[30] Foreign Application Priority Data

Jul. 19, 1989 [JP] Japan .................... 1-186637

[51] Int. Cl.$^5$ ............................................. G01N 27/00
[52] U.S. Cl. ................................. 422/65; 422/63; 422/67; 422/68.1; 436/47
[58] Field of Search .............. 422/63, 65, 67, 68.1, 422/107, 73; 436/43, 47, 50, 54, 526

[56] References Cited

U.S. PATENT DOCUMENTS

| | | | |
|---|---|---|---|
| 3,854,879 | 12/1974 | Figueroa et al. | 436/47 |
| 3,883,305 | 5/1975 | Hoskins et al. | 422/65 |
| 4,039,288 | 8/1977 | Moran | 422/65 |
| 4,168,775 | 9/1979 | Mueller | 198/795 |
| 4,315,891 | 2/1982 | Sakurada | 422/64 |
| 4,335,094 | 6/1982 | Mosbach | 436/526 |
| 4,528,159 | 7/1985 | Liston | 422/65 |
| 4,582,622 | 4/1986 | Ikeda et al. | 436/526 |
| 4,795,698 | 1/1989 | Owen et al. | 436/526 |
| 4,816,418 | 3/1989 | Mack et al. | 422/65 |
| 4,863,690 | 9/1989 | Berthold et al. | 422/65 |
| 4,937,048 | 6/1990 | Sakai et al. | 422/67 |
| 5,008,082 | 4/1991 | Shaw | 422/65 |

FOREIGN PATENT DOCUMENTS

| | | |
|---|---|---|
| 674288 | 6/1966 | Belgium . |
| 0212663 | 3/1987 | European Pat. Off. . |
| 0314525 | 5/1989 | European Pat. Off. . |
| 2152664 | 8/1985 | United Kingdom ............... 436/526 |

OTHER PUBLICATIONS

"The Abbott IMx Automated Benchtop Immunochemistry Analyzer System", 6027 *Clinical Chemistry* Sep. 34 (1988) No. 9, pp. 1726-1732, Washington, D.C. USA European Search Report.
Product Brochure: "This is Paramax, The Paramax Analytical System", American Dade, Division of American Hospital Supply Corporation, Miami, Fla., distributed by American Scientific Products, Division of American Hospital Supply Corporation, McGraw Park, Ill., published before Jun. 20, 1983, 12 pages.

*Primary Examiner*—James C. Housel
*Assistant Examiner*—Long V. Le
*Attorney, Agent, or Firm*—Sughrue, Mion, Zinn, Macpeak & Seas

[57] ABSTRACT

An automatic immunoassay analyzer includes first and second conveyors which support a plurality of speciment vessels and reaction vessels, respectively. Both conveyors are rotated synchronously and continuously in the same direction by first and second conveyor driving devices. A division-pouring device sucks a speciment from a specimen vessel stopped at a suction stage and pours a portion thereof into a reaction vessel stopped at a division-pouring stage. A holding device stops and holds one of the specimen vessels transferred into the suction stage for a predetermined time period in which the reaction vessel(s) holding measurement analytes to be tested for the respective specimen are transferred and stopped sequentially at the division-pouring stage. The analyzer reduces operator error, and ensures alignment of the reaction vessels with the appropriate specimen to be tested.

27 Claims, 7 Drawing Sheets

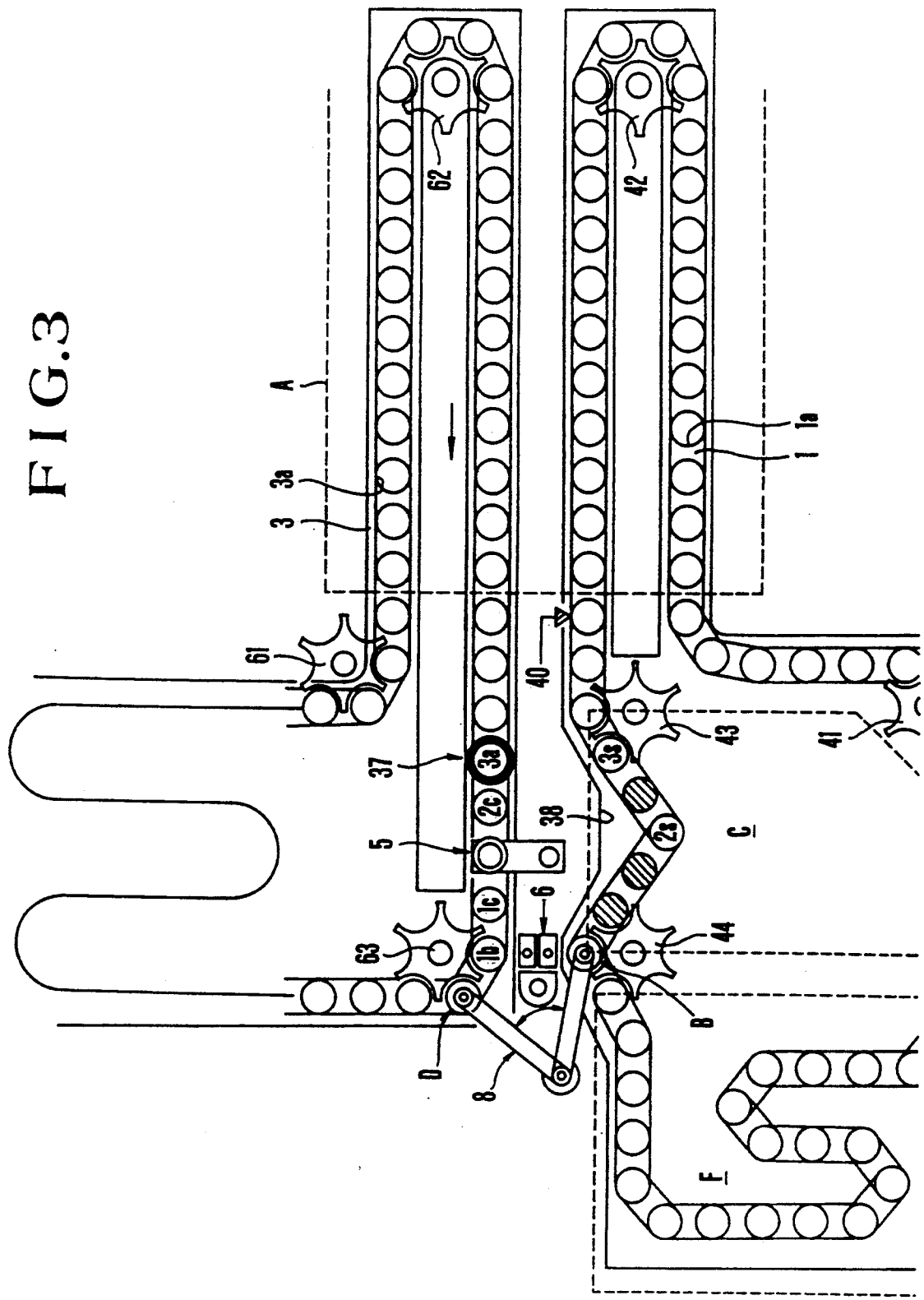

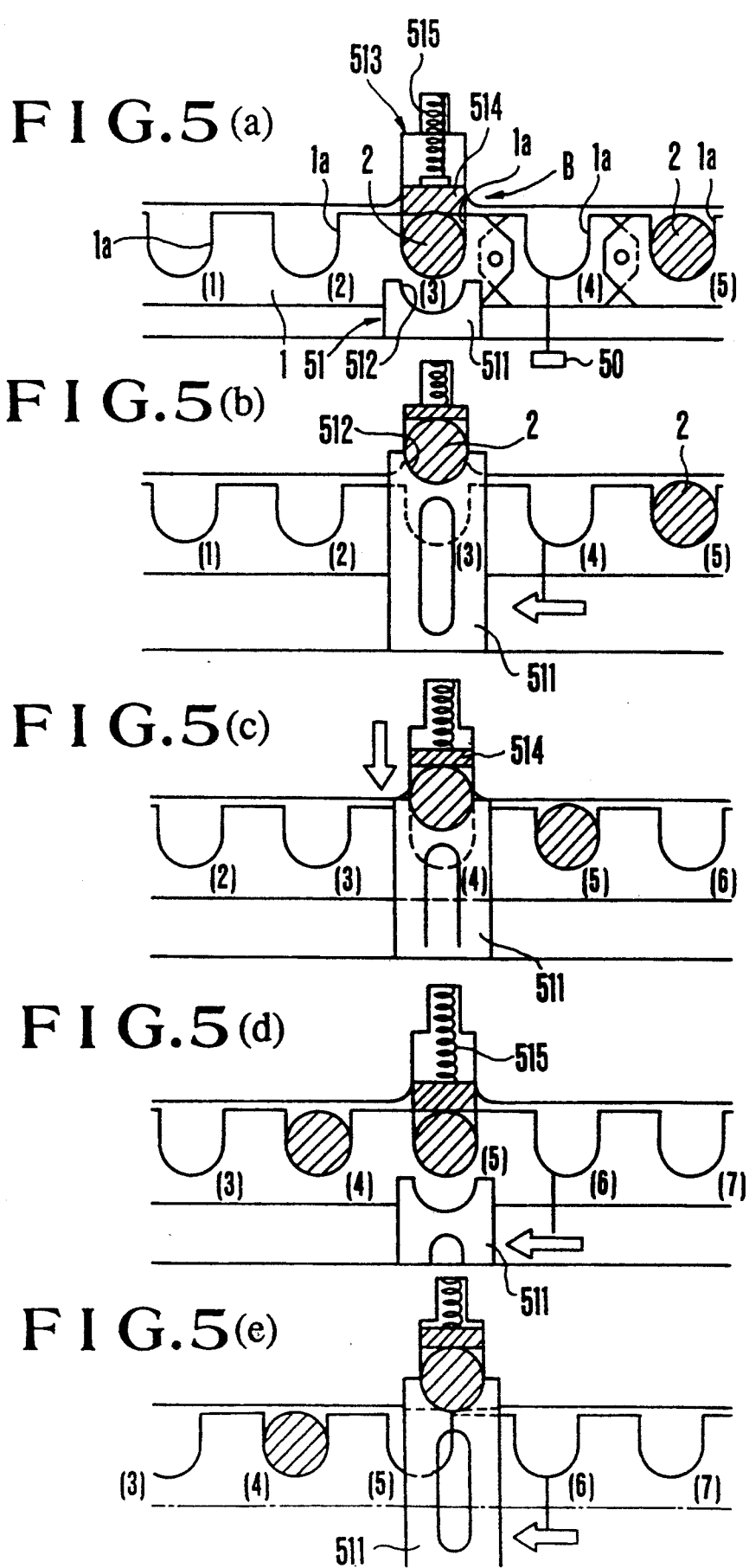

AUTOMATIC IMMUNOASSAY ANALYZER

This is a Continuation of application Ser. No. 07/554,507 filed on Jul. 19, 1990 now abandoned.

BACKGROUND OF THE INVENTION

1. Field of the Invention

This invention relates to an automatic immunoassay analyzer. More particularly, the present invention relates to an immunoassay analyzer capable of measuring automatically and continuously at least one measurement (clinical testing) analyte for each of a plurality of specimens (the specimens as the objects of measurement) and more in particular, to a multiple immunoassay analyzer having a random access function which can freely select the random measurement analytes for each specimen.

2. Description of the Related Art

Various immunological clinical testing methods have been developed in the past. An example of such methods is described in "KOUSO MENEKI SOKUTEI-HOU" (3rd edition) published by Igaku Shoin and "PRACTICE and THEORY of ENZYME IMMUNOASSAY", P. Tijssen, ELSEIER, AMSTERDAM, NEW YORK, OXFORD, and various methods are selected in accordance with the specimens of measurement and with the objects of measurement. Recently, a heterogeneous system has gained a wide application for achieving a high sensitivity measurement.

A method of measuring the quantity of an antigen contained in specimens such as blood collected as a specimen from a patient will be explained on the basis of a one-step sandwich method by way of example. In accordance with this method, the specimen as the object of measurement is added into a reaction vessel into which an antibody coupled to an insoluble support (solid phase) such as the inner wall of a synthetic resin vessel or particles (hereinafter referred to as the "immobilized antibody") and an antibody labeled by a label material such as a radioactive material, a fluorescent material, an enzyme, or the like (hereinafter referred to as the "labeled antibody") are in advance packed (so called sandwich). In the reaction vessel, the antigen contained in the specimen causes the antigen-antibody reaction with the immobilized antibody and the labeled antibody to form an antigen-antibody composite member and at the same time, the labeled antibody couples with this antigen-antibody composite member, thereby forming a composite member wherein the three components, that is, the immobilized - antigen - labeled antibody, are sandwiched.

In this manner the labeled antibody is coupled with the solid phase with the antigen in the specimen being the medium.

Next, the excessive labeled antibody which does not couple with the antigen added into the reaction vessel and the antibody components which do not participate in the immunological reaction other than the label coupled with this solid phase are subjected to isolation (hereinafter referred to as "B/F isolation"). Finally, the label quantity proportional to the antigen quantity coupled with the solid phase is measured quantitatively by physical or chemical means utilizing the properties of the label in order to determine the antigen concentration in the specimen.

In contrast, a two-step sandwich method carries out the first reaction by adding the specimen to the reaction vessel into which only the immobilized antibody is in advance charged, and then adds the labeled antibody to cause the second reaction.

In other words, the specimen is first added to the reaction vessel into which the immobilized antibody (or a reagent containing the same) is in advance charged. Thus, a specific antigen in the specimen causes the antigen - antibody reaction with the immobilized antibody and is coupled and fixed to the solid phase. The unreacted components which do not cause the antigen - antibody reaction are discharged outside the vessel through B/F isolation. Next, the labeled antibody is added to the reaction vessel so as to cause the antigen - antibody reaction. In this manner, the composite member of the immobilized antibody - antigen - labeled antibody is formed. The unreacted components and the reaction residue are subjected to B/F isolation and discharged outside the vessel.

After this operation, the amount of the composite coupled with the solid phase is measured by quantitative determination of the label material in the same way as in the one-step system described above so as to determine the antigen concentration in the specimen.

Besides these sandwich methods described above, a so-called "competitive method" is also known. This method causes the competitive reaction between the antigen in the specimen and the antigen labeled in advance by the label material (generally referred to as the "labeled antigen") at the same combined site of the immobilized antibody described above.

In accordance with this competitive method, the antigen in the specimen is reacted with the immobilized antibody and also the labeled antigen contained in the reagent is reacted with the immobilized antibody. Accordingly, the component (antigen) in the specimen as the object of measurement and the labeled antigen react competitively with the antigen - antibody reaction portion of the combined site of the immobilized antibody. As a result, the immunological composite members are formed respectively on the basis of the quantity ratio (concentration ratio) between the antigen component which is contained in the specimen and whose quantity is not known and the labeled antigen component whose quantity is in advance given. In this manner the antigen quantity in the specimen can be determined in accordance with the calculation proportional to the ratio described above by effecting the quantitative measurement of the quantity of the label material immobilized to the solid phase by utilizing the properties of the label material after B/F isolation of the unreacted materials and the reaction residue in the same way as the sandwich method.

As described above, the method of measuring quantitatively the quantity of the label material (which is sometimes referred to as a "marker") immobilized and coupled to the solid phase varies with the properties of the label material and according to the classification based on such an aspect, the immunoassay method is often referred to as FIA when a chemical fluorescent material is used for labeling, RIA when a radio-active material is used and EIA when an enzyme is used.

Detection and quantitative determination of trace amounts of living body materials and physiologically active substances by utilizing such immunological means are useful for diagnosis of various diseases and for the preparation of a remedial plan. For accurate diagnosis, the utilization of the analysis result of a plurality of different analytes is mostly effective and reagents and the like have conventionally been developed for measuring various living body components for the diagnosis of various diseases.

The immunological reaction measurement method used for the measurement of the physiologically active substances and the like utilizes in various manners the immunological reaction and the properties of the label material for measuring the antigen quantity either chemically or physically are also diversified. Accordingly, those apparatuses which have conventionally been developed for the measurement, particularly automated apparatuses having high industrial values, combine suitable methods and mechanisms in consideration of the measurement method of the immunological reaction and the problems peculiar to the properties of the label material, and a definite apparatus construction has been devised by further taking into consideration the feasibility of the apparatus when it is used in practice and the cost of the apparatus, equipment, operation, and the like. Recently, the development of a reagent kit for clinical diagnosis and apparatuses has drawn increasing attention and various attempts have also been made to design and construct such apparatuses.

However, most of the apparatuses that have conventionally been provided for these purposes do not sufficiently take into consideration the fact that the measurement operations are complicated because they need a large number of reagents such as peculiar immunological reagents, reaction reagents, reference specimens, and so forth, for the object material of measurement. For example, those apparatuses which have a large number of process steps which depend on the manual operation of a testing operator are not suitable for processing large quantities of samples.

Since the results of measurements are used directly as data for the diagnosis and foundation of the corresponding remedy, and since the remedial method varies with the measurements, an extremely high level of detection accuracy is required even though the apparatuses can deal with the measurement and quantitative determination of trace amounts of components, because the number of specimens requiring the testing operation described above which needs complicated and very careful attention and skill has tended to increase drastically in recent years but it is very difficult to maintain and secure a large number of skilled testing operators to meet such a large number of inspections. Accordingly, mistakes in inspection and accuracy management have become the critical problem.

For the reasons described above, the development of the apparatus which can eliminate as much as possible the errors and mistakes resulting from the individual difference of testing operators has been desired and the development of the automated apparatus which can rapidly process large quantities of specimens has also been desired.

As one of the automated immunological reaction measurement apparatuses for processing a large number of specimens in large quantities within a short period, an apparatus which processes batch-wise the measurement analyte common to a large number of specimens has been proposed in the past.

However, this batch processing system makes possible collective processing of only a specific analyte of measurement for a large number of specimens. Therefore, the number of measurement analytes is limited from the number of apparatuses, and the like. Though this system is effective when only a predetermined and constant analyte is tested, it is not suitable for the application wherein the measurement analytes are variously changed or selected. Furthermore, the system involves another problem that once the test for one analyte is started, the next inspection cannot be made till the end of the former. Moreover, the system is susceptible to the limitation of the operation because the specimens having the same measurement analyte must be gathered in order to improve efficiency of the collective processing of the single measurement analyte. For example, a large number of specimens gathered from various medical institutions and the like must be gathered and compiled once again in accordance with each measurement analyte, so that this compilation operation invites the drop of overall efficiency and induces the mistakes in the operation.

As an apparatus for solving such problems, a random access system apparatus having the following construction has been proposed (in Japanese Patent Laid-Open No. 148585/1987). Namely, a plurality of desired measurement analytes for each specimen are inputted and registered to an electronic control apparatus (a so-called "computer") and on the other hand, reaction vessels into each of which a reagent corresponding to each of these measurement analytes is in advance charged is selected. The reaction vessels are then placed in the sequence of the measurement analytes for each specimen on a tray (test plate) having m x n arranged openings, for example, and this tray is then fed into a measurement apparatus so as to carry out the measurement operation in accordance with the registered sequence described above.

This apparatus is advantageous because it can solve the problem of the conventional batch processing system in that the specimen aggregate must be formed in accordance with each measurement analyte.

However, the apparatus of the random access processing system requires the input and registration operation of the measurement analytes of each specimen by use of an input device such as a keyboard. In other words, though the apparatus can automate the operations after the start of measurement themselves, a great deal of burdensome are preparatory steps required manually before the start. Since the reaction vessels must be aligned on the tray in accordance with the registered sequence by use of the mechanized device, efficiency of the operation must yet be improved. Furthermore, the apparatus is likely to be expensive and the burden on equipment is great.

SUMMARY OF THE INVENTION

The present invention provides a novel apparatus which can solve the problems confronted by the various conventional apparatus described above, can cope easily with a large number of specimens even when their measurement analytes are different in various ways, can measure the analytes easily and rapidly and is suitable for a random access system.

It is another object of the present invention to provide a novel apparatus which can cope easily either with an apparatus having a relatively small number of specimens to be processed or with an apparatus having a considerably large number of specimens by the design change of conveyors while keeping the fundamental structure of the apparatus in common, and has high design freedom.

It is still another object of the present invention to provide a novel apparatus which can easily add the specimens even after the start of the measurement operation by the apparatus.

It is still another object of the present invention to provide a novel apparatus which can finish the manual work necessary for the measurement by merely aligning specimen vessels into which the specimens are charged and reaction vessels whose contents vary with the measurement analytes for carrying out the immunological reaction on respective conveyors and is therefore extremely easy to operate and is free from the mistake in the operation.

In order to accomplish the various objects described above, the inventors of the present invention have put specific importance on the mutual association between the specimen vessels and the reaction vessels, and have completed the present invention on the basis of the novel concept, which cannot be found in the conventional apparatuses, in that these specimen vessels and reaction vessels are aligned on two conveyors in association with one another.

Typically, the present invention is characterized by the apparatus which has the following construction.

The present invention provides an automatic immunoassay analyzer which comprises an endless specimen vessel transfer conveyor (hereinafter referred to as the "first conveyor") which is equipped sequentially with a large number of support portions consisting of openings, for example, (hereinafter referred to typically as the "openings") each for supporting one specimen vessel by fitting it in the transfer direction and is disposed in such a manner as to rotate from a first set stage disposed at a position where the operation of supporting the specimen vessels to the openings is carried out, to pass then through a suction stage where the specimen inside the specimen vessel is sucked by division-pouring means and to rotate and return back again to the first set stage; means for rotating the first conveyor, which determines sequentially the opening zone for each specimen by zoning the openings of the first conveyor by the number n (n: a positive integer and arbitrary for each specimen) of the measurement analytes required for each specimen supported on the conveyor, and transfers and stops sequentially these specimen vessels into and at the suction stage while the corresponding specimen vessel is being supported by any of the openings (most optimally, the leading opening) inside each zone; an endless reaction vessel transfer conveyor (hereinafter referred to as the "second conveyor") which has substantially the same construction as the first conveyor and the openings, rotates from a second set stage disposed as the operation position where the reaction vessels are supported one by one into the large number of openings, passes by a division-pouring stage where the specimen sucked from the specimen vessel by the division-pouring means is dividedly poured into the reaction vessel, then passes through a reaction-measurement stage where the immunological reaction inside the reaction vessel and the measurement of the reaction are carried out, and rotates and returns once again back to the second set stage; second conveyor driving means which transfers, stops and feeds out sequentially these reaction vessels into, at and from the division-pouring stage while the reaction vessels corresponding to the measurement analytes of each specimen are being supported by the openings of the reaction vessel transfer conveyor; division-pouring means which sucks the specimen from the specimen vessel stopped at the suction stage and pours it dividedly into the reaction vessel stopped at the division-pouring stage; and holding means which holds the corresponding specimen vessel transferred to the suction stage under the stop condition for the period in which the reaction vessels corresponding to each specimen are sequentially transferred and stopped into and at the division-pouring stage.

The reason why the present invention employs the structure wherein the specimen vessels are supported skippingly by the openings disposed on the first conveyor and the reaction vessels are continuously supported by the openings aligned on the second conveyor without any gap by use of these two conveyors described above in order to carry out the immunoassay operation is as follows.

Generally, a plurality of measurement analytes selected in accordance with requirements are designated for the specimen added into the predetermined specimen vessel for mutually different diagnosis. Mostly, the content of the measurement analyte itself and the number of analytes vary from specimen to specimen. In such a case, the opening zone corresponding to the number of measurement analytes (e.g. A, B, C) of the first specimen is determined in the first conveyor (specimen vessel transfer conveyor) by counting the openings of the conveyor stopped at the first set stage from the leading opening to the third opening and stipulated as the zone for the first specimen (the first zone) and the corresponding first specimen vessel is fitted into the leading opening. Next, the openings in the number corresponding to the number of measurement analytes of the second specimen are counted from the next opening (the fourth opening from the leading opening of the first set stage) and are stipulated as the second opening zone. The corresponding second specimen is fitted into the leading opening of this zone. Similarly, the third specimen vessel is fitted into the leading opening of the third opening zone, the fourth specimen vessel is fitted into the leading opening of the fourth zone, and so forth. In this manner, the vessels are set to the first conveyor.

In the second conveyor (the reaction vessel transfer conveyor), on the other hand, the reaction vessels corresponding to the measurement analytes (e.g. A, B and C described above) of the first specimen are fitted one by one into the openings from the leading opening of the conveyor which is stopped at the second set stage. For example, the reaction vessel A to which a specific reagent for the immunological measurement of A is charged is fitted into the leading (first) opening, and the reaction vessels B and C are fitted to the second and third openings, respectively. Then, the reaction vessels corresponding to the measurement analytes designated for the second specimen are sequentially fitted into the subsequent openings (from the fourth opening counted from the leading opening of the second set stage), and similarly, the reaction vessels are sequentially fitted for the third specimen and so forth.

According to this arrangement, the fitting work of the vessels into the openings of these two conveyors can be made easily. In other words, only one corresponding specimen vessel is supported in the opening zone zoned by the number of measurement analytes of each specimen on the first conveyor. Therefore, if the corresponding reaction vessels are fitted into the openings on the second conveyor having similar openings in registration with the specimen vessel fitting openings of the first conveyor and the subsequent empty openings (into which the vessels are not fitted), the position relationship between one specimen and the corresponding reaction vessels (generally, plural vessels) does not collapse for each specimen but can be always maintained as such.

If the first and second conveyors are rotated synchronously while keeping the position relationship between the specimen vessels and the reaction vessels as described above and if the timing at which the specimen vessels are stopped at the suction stage in the first conveyor and the timing at which the reaction vessels are stopped at the division-pouring stage in the second conveyor are controlled, division pouring can be effected suitably by use of a simple division-pouring mechanism, and additional fitting of the specimen and reaction vessels at the set stages can be made freely. Thus, random measurement for each specimen and the addition of the specimen as the objects of the present invention can be accomplished easily and reliably.

In a preferred embodiment of the set stage where each of the vessels described above is fitted, the reference position of the leading opening is determined in each of the first and second set stages, and display plates of the opening numbers are disposed along each conveyor towards the upstream side of the transfer path from this reference position so that the display numbers are put to the openings such as Nos. 1, 2, 3, 4, and so forth from the opening at the reference position. This arrangement provides the advantage in that when the specimen vessels are fitted into the skipping openings in the first conveyor, it becomes possible to recognize easily and visually that the opening next to the opening having the last display number into which the reaction vessel of the second conveyor is fitted is the opening into which the next specimen vessel is to be fitted. For example, if the display number of the last reaction vessel fitted into the opening of the second conveyor in such a manner as to correspond to the second specimen is No. 10, the opening in the first conveyor into which the third specimen vessel is to be fitted can be easily confirmed to be the opening No. 11.

It is also possible to dispose additionally lamp means such as LEDs to the display plate of the opening No. disposed along each conveyor so that the opening No. into which the next specimen vessel is to be fitted is turned ON by utilizing the signal from input means for inputting the number of measurement analytes which will be described elsewhere.

If the vessels fitted into the openings of the two conveyors are fed out from the respective set stages having the structure described above by driving the conveyors in synchronism with each other, the vessels can further be added reliably to the conveyors without inviting any mistakes of operation.

The automatic immunoassay analyzer of the present invention explained typically by the construction described above can exhibit further excellent effects by employing the structure wherein two conveyors having a large number of vessel support portions with mutually equal gaps are juxtaposed with each other at the first and second set stages that are juxtaposed with each other, too. According to this arrangement, both of the specimen and reaction vessels have the juxtaposition relationship when the specimen vessels and the reaction vessels are supported by the first and second conveyors, respectively, and the operator can confirm them more reliably and more easily.

The two conveyors in the present invention are preferably an endless chain type conveyor capable of zigzag motion inside a horizontal plane so as to minimize the capacity of the apparatus. Particularly the use of the conveyor capable of zigzag motion for the first conveyor is recommended when the first conveyor is fed out from the set stage in synchronism with the second conveyor. In other words, the first conveyor in the present invention must be kept stopped at the suction stage for the period of division-pouring of the specimen into a plurality of reaction vessels. In this case, the first conveyor can be kept staying in the zigzag form at a suitable position of the transfer path by utilizing its property of being capable of zigzag motion. For, the zigzag motion described above can mechanically absorb the time deviation between the intermittent feed operation of the conveyor from the set stage with a time interval "t" for each period and the holding operation of the specimen vessel at the suction stage for the period "n"×"t".

As a mechanism for stopping and holding the specimen vessel supported by the first conveyor at the suction stage for the period "n"×"t", it is possible to use, for example, a mechanism which stops the sprocket disposed on the suction stage among those which are disposed for the rotation of the conveyor for the period (n×t) corresponding to the number of measurement analytes designated for the specimen. In this case, the sprocket kept at the portion of the suction stage until the next specimen vessel is transferred into the suction stage must be rotated continuously in such a manner as to apply the feed of n times corresponding to the rest at the timing of the intermittent driving of the second conveyor for transferring and stopping the next reaction vessel to and at the division-pouring stage after the passage of this period (n×t). The stays for the zigzag motion of the first conveyor are preferably disposed upstream and downstream of the suction stage of the first conveyor lest any problem occurs in the movement of the conveyor due to the motion of the sprocket described above.

The mechanism for stopping and holding the specimen vessel at the suction stage for the predetermined period in the present invention is not particularly limited to the mechanism described above, but other systems can be employed, too. For example, it is possible to employ the mechanism wherein the specimen vessel transferred to the suction stage is taken down from the conveyor and the conveyor passing through the suction stage is rotated intermittently in the same way as at other portions. After suction is complete, the specimen vessel may be discharged outside the apparatus by exclusion means because its function is already complete, or may be returned to the empty opening of the conveyor. If this arrangement is employed, it is not particularly necessary to make stop-holding control of the conveyor at the suction stage and either to dispose the zigzag stay portion. As an example for taking down the specimen vessel from the conveyor, it is possible to use a mechanism, for example, wherein the opening of the conveyor is formed in a sidewardly open shape and a reciprocating plunger is operated in the interlocking arrangement so as to push out the vessel sidewardly at this suction stage.

In the present invention, the number of measurement analytes designated individually for each specimen must be utilized as the control information in the control mechanism for stopping the rotation of the sprocket at the suction stage and for causing the continuous rotation after the stop or in the mechanism for taking down the specimen vessel from the conveyor, in order to stop the specimen vessels transferred by the first conveyor at the suction stage for the period corresponding to the number "n" of the measurement analytes. Such control information can be inputted to the apparatus by various methods.

For example, it is possible to employ the system which disposes an input ten-key (input means for inputting the number of analytes) and inputs the number of the measurement analytes when the specimen is supported onto the first conveyor and a system which disposes optical counter means or counting the specimen vessels and the number of subsequent openings, downstream of the set stage of the first conveyor. In the latter system using the counter means using the counter, it is most appropriate if the specimen vessel is supported by the leading opening of each zone in order to count the number of openings inside each opening zone determined on the first conveyor and in this case, control of suction, division-pouring, etc. becomes easy, too.

Besides the construction described above, the following construction is preferably added in the present invention.

One of such structures is one wherein information relating to the name of a medial institution or personal information of the specimen (name, measurement analytes) is in advance put to the specimen vessel or is recorded magnetically, and is read by first read means disposed at an intermediate portion of the transfer path of the conveyor (preferably, upstream of the suction stage). A definite example of the display of the specimen vessel and the read means includes the combination of a character display with an optical reader, the combination of a bar code printout with a bar code reader or the combination of a magnetic recording medium with a magnetic reader. Those displays of the vessels which are recorded at the time of specimen collection in a hospital are preferably made available.

Besides the utilization described above, the specimen information read by the first read means can be inputted to an electronic controller such as a microprocessor and can be utilized for the display of the measurement result at the post-stage, and can also be utilized in order to confirm that any testing mistake does not occur by comparing the measurement analytes, which are read information of the second read means and are actually measured values, with a comparison program in the electronic controller described above, for example.

Another preferred additional construction of the present invention is the structure wherein necessary information such as the measurement analytes is in advance displayed on the reaction vessel or is magnetically recorded and is read by the second read means disposed at an intermediate portion of the transfer path of the conveyor (preferably upstream of the division-pouring stage). The same definite structure as that of the first read means described above can be used as the combination of the displays on the specimen vessels with the read means. The information on the measurement analytes that is read by the second read means is inputted to the electronic controller such as the microprocessor and is used for the display of the measurement result in the same way as in the first read means, or can be used for comparison and collation with the measurement analytes designated for the specimen vessel and read by the first read means. Furthermore, the read information relating to the measurement analytes and displayed on the reaction vessel can be utilized effectively for selecting operation modes of various mechanisms at the reaction-measurement stage (such as a reagent division-pouring mechanism, a substrate division-pouring mechanism, etc.) when the reagents used in these mechanisms are different.

In the present invention, the known immunoassay method can be as such used fundamentally as the operation which is carried out when the second conveyor passes by the reaction-measurement stage, and various improvements can of course be applied in order to operate more effectively the mechanism of the present invention. One-step or two-step sandwich method using the enzyme label is preferably used as the immunological reaction measurement system, though it is not particularly limitative.

The structure of the typical reaction-measurement stage of the present analyzer employing such a sandwich method will be explained briefly. An example of the analyzer of the one-step system is equipped wit the following mechanisms downstream of the division-pouring stage for dividedly pouring the same into each reaction vessel:

(1) a diluted solution division-pouring mechanism for dividedly pouring a specimen diluted solution into the reaction vessel;

(2) a temperature control mechanism for effecting the immunological reaction (incubation, stirring) in the reaction vessel;

(3) a B/F isolation mechanism for isolating the reacted components and the unreacted components; and (4) a measuring instrument for measuring the optical power of the solution in the reaction vessel.

Incidentally, the division-pouring mechanism of the division-pouring stage can be used also as the diluted solution division-pouring mechanism.

In the case of so-called EIA using the enzyme as the label in the apparatus having the construction described above, a substrate division-pouring mechanism is used at a pre-stage of the optical measuring instrument (4).

The operation of the automatic enzyme immunoassay analyzer of the present invention will be explained stepwise about the case where the analyzer has the construction described above and the reaction and measurement are carried out by the one-step system, by way of example.

At the first step, each reaction vessel into which the fixed antibody and the antibody labeled by the enzyme are in advance charged is conveyed and transferred to the division-pouring stage by the second conveyor. On the other hand, the corresponding specimen vessel is transferred to the suction stage (or is kept continuously stopped at the suction stage from the division-pouring stage for the previous reaction vessel), and suction of the specimen from the specimen vessel and division-pouring of the sucked specimen into the reaction vessel, and if necessary, division-pouring of the diluted solution, are carried out by a movable pipet device as the division-pouring means, for example. In this manner, the composite member of the fixed antibody - antigen - labeled antibody is formed inside the reaction vessel. Next, at the second step, other excessive reagents and the specimen are subjected to B/F isolation while leaving the composite member described above in the reaction vessel, and the substrate solution of the label enzyme is dividedly charged into the reaction vessel at the third step.

At the fourth step, the change of the substrate generated by the enzyme activity (e.g. the change of coloring of the colorless substrate due to decomposition) is measured by the optical measuring instrument and the result of measurement is recorded in the recording unit such as the electronic controller. The result of measurement is also printed out by a suitable printer, or the like, and the measurement is thus complete. The operations described above are effected repeatedly for each specimen and for each measurement analyte.

As can be understood from the explanation given above, the analyzer of the present invention can automatically carry out all the operations other than the operation of supporting manually the specimen vessels on one of the conveyors in the intervals designated by the number of measurement analytes and the operation of supporting manually the reaction vessels on the other conveyor, by the mechanized devices. Moreover, since the various devices necessary for the immunoassay are disposed at the intermediate portions of the transfer path for rotating intermittently the two conveyors so that the operations for the stopped vessels can be made by the mechanical devices, each mechanism can be constituted easily as an independent mechanism.

Accordingly, the basic construction of the analyzer explained in the typical sequence of processing steps described above can have extremely high design freedom in that the analyzer can be changed in design and for the objects of use in various ways without changing the construction that the two conveyors are rotated. To change the analyzer to the two-step system, for example, the second B/F isolation mechanism can be disposed easily and the mechanism for dividedly charging the labeled antibody, and in the analyzer having the mechanism for such a two-step system, it is possible to operate the analyzer as the one-step system by stopping the corresponding mechanism.

The intermittent feed timing of the conveyors in the analyzer in the present invention may be determined with the necessary time of the mechanism having the longest operation time, among the various mechanisms disposed along the transfer path, being the reference.

The transfer path can be constituted by combining, for example, a flat plane on which the conveyors such as the endless chain conveyors are disposed and which provides the rotating surface for them, sprockets for rotating the conveyors, rotation belts, cam mechanisms, and other driving mechanisms. Suitable temperature control units are preferably disposed along the transfer path in order to keep a suitable temperature for the immunological reaction and the enzyme reaction in the transfer mechanism.

Various kinds of reaction vessels are prepared as the reaction vessels used in the present invention. The solid phases to which the antibody or the antigen is fixed are packed into the vessels and different object substances (physiologically active substances, etc.) in the specimen as the object of measurement are packed into different reaction vessels. In the case of the one-step system, the reaction vessel into which the labeled antibody is also packed in advance is also prepared. Furthermore, the opening of each reaction vessel is preferably sealed by an aluminum foil, for example, lest foreign matter mix during normal storage, and printing of the codes of the measurement analyte names onto this sealing foil is recommended as a preferred embodiment of the invention.

When such a reaction vessel of the foil seal type is used, a seal break mechanism is preferably disposed upstream of the division-pouring stage of the second conveyor and a known mechanism can be used as such a seal break mechanism.

The specimen division-pouring means described above is not particularly limitative. Generally, a typical example of such means is a movable pipet device which sucks the specimen from the specimen vessel transferred and stopped to and at the suction stage and then moves to the division-pouring stage so as to charge dividedly the sucked specimen into the reaction vessel. The movement of the pipet device may be either parallel motion or rocking, and an elevation mechanism capable of lowering into the vessel is preferably disposed, whenever necessary. It is further preferred to dispose a pipet washing well, a diluted solution port, and the like, in the moving path of this pipet device and to connect a solution supply device for supplying the diluted solution, the washing solution, etc., to this pipet device.

The incubator mechanism (2) for effecting the immunological reaction (temperature control, stirring) explained about the typical analyzer described above is appropriately disposed as part of the conveyor transfer path downstream of the division-pouring stage. This incubation mechanism can be constituted fundamentally by disposing the transfer path having an incubator mechanism and a predetermined length but preferably, magnetic means for causing a vibrating magnetic field to act on the transfer path is disposed by packing the magnetic particles into the reaction vessel. For, stirring can thus be imparted to the solution inside the reaction vessel. The magnetic particles can be used also as the solid phase for fixing the immobilized antibody, and the like.

Though its structure is not particularly limitative, the B/F isolation mechanism is suitably of the type in most cases wherein the washing solution is dividedly poured from the jet nozzle into the reaction vessel and the solution is sucked and discharged by the suction nozzle.

An optical photometer, for example, which is disposed at the final stage of the reaction-measurement stage is to measure an enzyme or a fluorescent material when the label of the labeled antibody is the enzyme or the fluorescent material and a radioactive ray sensing type measuring instrument is used when a radioactive material is used as the label. A top-top type optical photometer is recommended so as to make the construction of the automatic immunoassay analyzer simple.

Generally, an electronic controller using a microprocessor is used in order to operate the analyzer of the present invention. This electronic controller can be constituted by use of known electronic circuit technique but in the case of the analyzer of the present invention, timing control is preferably made by a main computer, for example, and the operation of each mechanism is preferably controlled dividedly by a local microprocessor in accordance with a predetermined sequence program because mutual control information are not fundamentally necessary except that the intermittent drive control of the conveyor, the rest control of the sprockets at the suction stage and the control of various mechanisms at the reaction-measurement stage must be controlled at the associated timing between them. According to this system, the control of the common mechanisms is left unchanged and only the change portions are replaced or corrected so as to cope with any design change.

The control system necessary for the analyzer of the present invention typified as above can be provided by a definite sequence program assembled in advance in the local processor for operating the individual mechanisms and by setting of the timings for establishing the timing between the start timing of the operation of each mechanism based on the program and the intermittent driving of the conveyors. More definitely, it is possible to employ a system, for example, which holds the input information from the first read means (or the input device such as the ten-key described already) and from the second read means by a shift register and provides sequentially the operation timing of each mechanism by counting the operation of intermittent driving of the conveyors. The operation sequence of each mechanism can be provided by programming the operations given in the explanation described above.

BRIEF DESCRIPTION OF THE DRAWINGS

FIG. 3 is an explanatory view useful for explaining the structure and movement of each container 2, 4 set in the set stage A of the analyzer while it is transferred to a suction stage B and a division-pouring stage D;

FIGS. 5(a)–5(e) are explanatory views useful for explaining the structure and sequential movement at the suction stage B of the third embodiment of the present invention.

DESCRIPTION OF THE PREFERRED EMBODIMENT

Hereinafter, the present invention will be explained in detail with reference to preferred embodiments thereof shown in the accompanying drawings.

EMBODIMENT 1:

FIGS. 1 to 4 show the embodiment wherein the present invention is applied to an immunoassay method (EIA) using an enzymic label of a two-step system. Accordingly, this embodiment uses each reaction vessel into which a fixed antibody prepared by fixing an antibody to a solid phase (the solid phase being magnetic particles in this embodiment) is packed in advance. Though the fixed antibody such as described above is used for the antigen measurement, a fixed antigen may of course be used for the antibody measurement.

Figure 1:
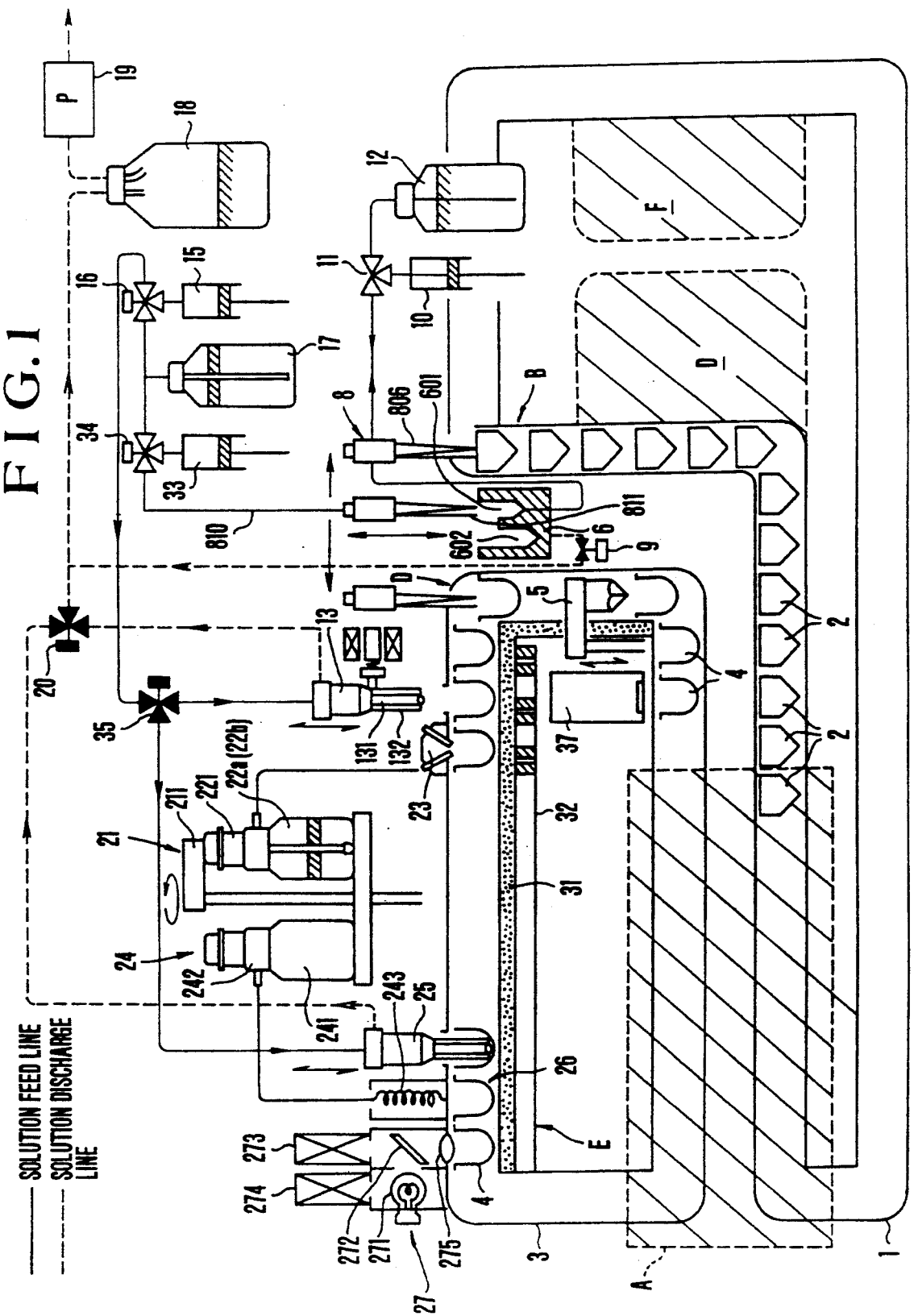
FIG. 1 is an explanatory view useful for explaining the outline of the structure of an analyzer in accordance with one embodiment of the present invention.

FIG. 1 is an explanatory view useful for explaining the outline of the structure of the analyzer of this embodiment. Reference numeral 1 represents a first conveyor (specimen vessel transfer conveyor). This conveyor 1 has thereon a large number of opening (support portions) 1a formed with predetermined gaps between them, and is driven intermittently with a predetermined time interval t by a driving mechanism, not shown in FIG. 1, to rotate along the rotating orbit ranging from the set stage represented by symbol A in the drawing and return again to it through a suction stage B. The first conveyor 1 in this embodiment consists of a endless chain type capable of zigzag motion as will be explained later with reference to FIG. 2 and is disposed in such a manner as to possess a stay C where it stays in the zigzag form between the set stage A and the suction stage B. Symbol F represents another stay which is disposed downstream of the suction stage B and at which the first conveyor stays in the zigzag form.

A large number of members 2, 2, 2 on the first conveyor 1 in FIG. 1 are specimen vessels. Though the specimen vessels are shown supported by all the openings 1a, 1a, 1a, . . . (not shown in FIG. 1) for fitting the specimen vessels for the sake of convenience, they are skippingly fitted into and supported by the openings 1a, 1a, 1a, . . . in practice. This point will be explained in further detail with reference to FIG. 3.

Reference numeral 3 represents a second conveyor (reaction vessel transfer conveyor). The second conveyor 3 in this embodiment has the same structure as the first conveyor 1 described above and has a large number of openings 2a (not shown in FIG. 1) formed with predetermined gaps between them in the transfer direction for supporting the reaction vessels 4. This conveyor 3 is driven intermittently by a driving mechanism not shown in the drawing with a predetermined time interval t so as to move along an endless orbit ranging from the set stage A and coming back again to the set stage A through a division-pouring stage D and then through a reaction-measurement stage E where an incubator heater 31 is disposed. The second conveyor 3 in this embodiment, too, consists of the endless chain type capable of zigzag motion. Incidentally, the set stages of the first and second conveyors 1 and 3 are represented in common by the symbol A. The incubator heater 31 in this embodiment may be of such a type which is produced by bonding a sheet-like heat generator to the lower surface of a flat sheet which forms the transfer path, and a current is caused to flow through this heat generator so as to control the temperature to a predetermined temperature. According to such a structure, the thermostat mechanism can be constituted very easily.

Figure 6A:
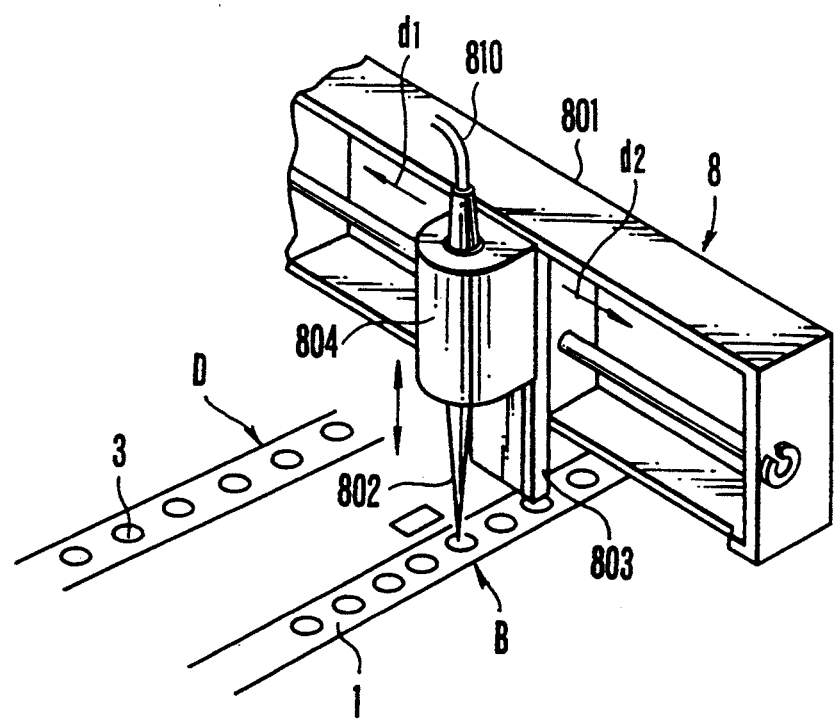
FIGS. 6(a) and 6(b) are perspective views of pipet devices used in the present invention, respectively.
Figure 6B:
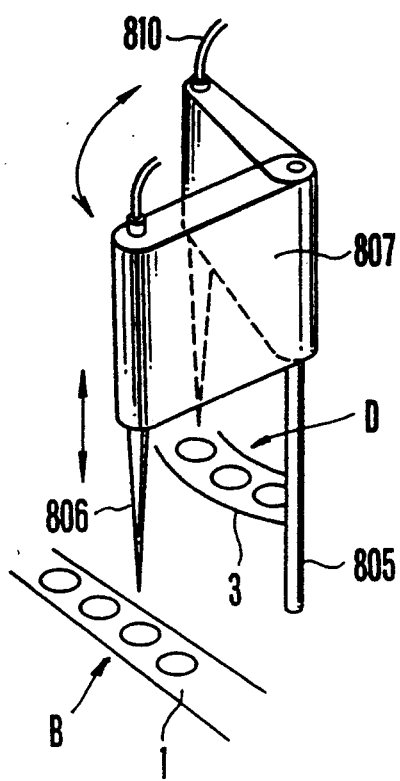

In the construction described above, the suction stage B disposed for the first conveyor 1 and the division-pouring stage D disposed for the second conveyor 3 are arranged in proximity of each other so that the suction and division-pouring operations of the specimen can be carried out between them. Namely, a pipet device as the division-pouring means represented by reference numeral 8 sucks a suitable amount of specimen from the specimen vessel 2 transferred to and stopped at the suction stage B and pours it dividedly into the reaction vessel 4 of the division-pouring stage D. The devices having the structures shown in FIGS. 6(a) and 6(b) can be used as the pipet device 8, for example. In the device structure shown in FIG. 6(a), a holder 804 which is integral with a pipet nozzle 802 is supported by a horizontal slide rack 801 in such a manner as to be slidable horizontally in a $d_1-d_2$ direction and is further supported by a vertical slide rack 803 in such a manner as to be slidable vertically. In the structure of the pipet device shown in FIG. 6(b), a holder 807 which is integral with a pipet nozzle 806 is supported at the upper end of a vertical shaft 805 capable of moving up and down and also capable of rotating around an axis so that the pipet nozzle 806 sucks and pours dividedly the specimen due to the vertical motion and rotation of this vertical shaft 805.

Turning back again to FIG. 1, the pipet nozzle 802 (or 806) of this pipet device is connected to a cylinder pump 33 for sucking and discharging a solution through a flexible tube 810 and this cylinder pump 33 is connected to a washing solution tank 17 of the pipet nozzle through a three-way electromagnetic valve 34 so that the nozzle can be washed by supplying and jetting the washing solution to the nozzle after completion of the suction and divided pouring of the specimen.

A diluted solution port 6 is disposed between the suction stage B and the division-pouring stage D where the pipet device moves, and a suitable amount of a diluted solution is supplied to a diluted solution well 601 of this diluted solution port 6 from a diluted solution reservoir 12. Reference numeral 10 represents a cylinder pump for supplying the diluted solution and 11 is a three-way electromagnetic valve. Reference numeral 602 represents a waste liquor portion of the diluted solution port, which discharges the diluted solution flowing out from the diluted solution reservoir 601 in the overflow system to a waste liquor tank 18. The tip portion of the pipet nozzle 802 (or 806) can be washed by causing the diluted solution to flow in the overflow system while the pipet nozzle 802 (or 806) is being dipped into the diluted solution well 601. Reference numeral 19 represents an exhaust pump for causing solution suction force to act on the waste liquor tank 18 and reference numeral 9 represents an electromagnetic valve disposed in the waste liquor path.

The operations of the division-pouring means inclusive of the pipet device having the structure described above are executed by the instruction of a local microprocessor (not shown) to which a sequence program for the series of operations is in advance set. In other words, when the corresponding specimen vessels 2 and reaction vessels 4 are stopped at the respective suction stage B and division-pouring stage D by the intermittent rotation of the first and second conveyors, the operation of the division-pouring means is started from the instruction from a main computer not shown in the drawing. The following operations a-d are repeatedly carried out whenever the specimen is dividedly poured:

a. The pipet nozzle 802 (or 806) is lowered into the diluted solution reservoir 601 of the diluted solution port 6 and sucks the diluted solution.

b. Next, the pipet nozzle 802 (or 806) is moved to the suction stage B and sucks the specimen from the specimen vessel 2.

c. The pipet nozzle 802 (or 806) is moved to the division-pouring stage D, where it charges dividedly the sucked solution (the specimen and the diluted solution) into the reaction vessel 4.

d. The pipet nozzle 802 (or 806) is moved to the waste liquor portion 602 of the diluted solution port 6 and is washed by causing the washing solution from the washing solution tank 17 to flow.

Incidentally, a level sensor 811 is disposed along the pipet nozzle 802 (or 806) and can detect a signal for controlling the vertical motion of the pipet nozzle 802.

Reference numeral 5 represents a seal-break mechanism disposed upstream of the division-pouring stage D of the second conveyor 3. It is used when a cup-type reaction vessel whose upper surface opening is sealed by an aluminum foil, for example, is used. More definitely, a mechanism which breckes the foil by moving up and down a rod-like member having a wedge-shaped sharp lower end is employed, for example.

The reaction vessel 4 into which the specimen is dividedly charged is next transferred to the reaction-measurement stage E by the intermittent rotation of the second conveyor 3 and incubation is effected for a predetermined time under the condition given by the incubator mechanism 31. In this incubation mechanism of this embodiment, the oscillating magnetic field by a magnetic plate 32 is caused to act on the reaction vessel together with the temperature control by the thermostat mechanism described above. The magnetic plate 32 in this embodiment can be disposed as a type wherein permanent magnets are fixed to a bar extending to the right and left in FIG. 1 with predetermined gaps between them and this bar is reciprocated to the right and left with a predetermined amplitude. In this manner, the vibrating magnetic field is caused to act on the magnetic particles (not shown) as the solid phase to which the fixing antibody, which is packed into the reaction vessel, is coupled and the solution inside the reaction vessel can be stirred.

After the incubation is made for the predetermined period, the reaction vessel 4 is then placed at the first B/F isolation mechanism 13 where the reaction residues, and the like, are removed. Incidentally, the portion between the division-pouring stage D and the first B/F isolation mechanism 13 is shown as a short transfer path in FIG. 1, but the length of this transfer path can of course be set to a suitable length in accordance with the time necessary for incubation.

In this first B/F isolation mechanism 13, a B/F probe has a double pipe structure and moves up and down, the washing solution is supplied into its center inner pipe 131 and suction force is caused to act from between the inner pipe 131 and its outer pipe 132 so as to suck and discharge the solution inside the reaction vessel. In other words, the inner pipe 131 is connected to the washing solution tank 17 through three-way electromagnetic valves 35, 16 so that the washing solution can be supplied from the tank 17 by the cylinder pump 15. The outer pipe 132 is connected to the waste liquor tank 18 through a three-way electromagnetic valve 20. Incidentally, the probe of the B/F isolation mechanism need not particularly be limited to the double pipe structure described above but may be of a type wherein a solution feed pipe and a solution discharge pipe are fitted into the reaction vessel in parallel with each other, for example.

Next, the reaction vessel 4 is transferred to a reagent division-pouring position 23 and a predetermined reagent, which is designed in accordance with each measuring analyte of the reaction vessel, is charged dividedly from the reagent division-pouring mechanism 21. The reagent division-pouring mechanism 21 of this embodiment has the following structure, for example. A plurality of reagent tanks 22a, 22b, . . . are arranged on a predetermined concentric circle and each reagent tank is equipped with a manual push type pump 221 so that a lever 211 capable of selecting its position by the rotation system can feed the solution when it is moved down. The selection of the reagents by the rotation of this lever 211 and the timing of its downward movement are selected in accordance with the sequence program set in advance to the local microprocessor (not shown) in accordance with the content of the measurement analyte which is read by a later-appearing second reader and with the operation signal of the intermittent rotation of the first conveyor.

The lever 211 of the reagent division-pouring mechanism in this embodiment is used also as the operation portion of a later-appearing substrate division-pouring mechanism 24.

In the reaction vessel 4, therefore, the immunological reaction takes place between the fixed antibody coupled to the surface of the magnetic particles which are packed in advance into the reaction vessel, the antigen contained in the specimen (the substance as the object of measurement and inspection) and the labeled (enzyme) antibody in the reagent added to the reaction vessel, and a composite member of the fixed antibody - the antigen - the labeled antibody is formed.

Next, the reaction vessel 4 is transferred to the position of the second B/F isolation mechanism 25, where the reaction residues, and the like, are removed. This second B/F isolation mechanism 25 may have exactly the same structure as that of the first B/F isolation mechanism 13 described already.

Next, the substrate is dividedly charged into the reaction vessel 4 by the substrate division-pouring mechanism 24 at the substrate division-pouring position. This substrate division-pouring mechanism 24 supplies the substrate into the reaction vessel through a thermostat portion 243 consisting of a coil-like pipe by the pump 242 of the manual push type which is operated by the lever 211 from the substrate tank 241 as described above. The thermostat portion 243 consisting of the coil-like pipe is constituted, for example, by passing a heating wire (not shown) through the center of the coil-like pipe so as to control the temperature of the substrate to be charged dividedly by temperature control means not shown in the drawing. The substrate may be single if the kind of enzyme used as the label is only one, but when different kinds of enzymes are used, a plurality of substrate tanks 241 (each having integrally the pump 242) and storing therein the different substrates may be disposed on the same concentric circle as that of the tanks of the reagent division-pouring mechanism described already.

The reaction vessel 4 into which the substrate is dividedly charged in this manner is then transferred to a fluorescent measurement position so as to measure the fluorescence emitted from the substrate by a photometer 27. This photometer 27 comprises, for example, a cold cathode discharge tube 271, a dichroic mirror 272, a signal detector 273, a reference detector 274, a lens 275, and the like.

In this manner the optical change generated by the reaction between the labelling enzyme (whose quantity is in proportion to the amount of the antigen contained in the specimen) coupled to the fixed antibody inside the reaction vessel and the substrate is measured, and this photometric data is inputted to the main computer, not shown in the drawing, to calculate the concentration of the intended object matter.

This calculation value is stored in a storage or outputted as hard copy data by output means such as a printer, whenever necessary. In this case, read data of later-appearing first and second readers may of course be recorded or outputted as the display analytes of the measurement value.

After this photometry is complete, the reaction vessel is returned to the set stage A with the rotation of the conveyor but generally, it is advisable to discharge it outside the analyzer by disposing a vessel discharging mechanism, not shown in the drawing, at an intermediate portion of this return transfer path. This vessel discharge mechanism is preferably disposed for the specimen vessels on the first conveyor 1 in the same way.

The explanation given above explains the outline of the structure of the immunoassay analyzer of the present invention and the outline of its operation. Next, the detail structure and operation of each portion will be explained in further detail with reference to FIG. 2 et seq.

Figure 2:
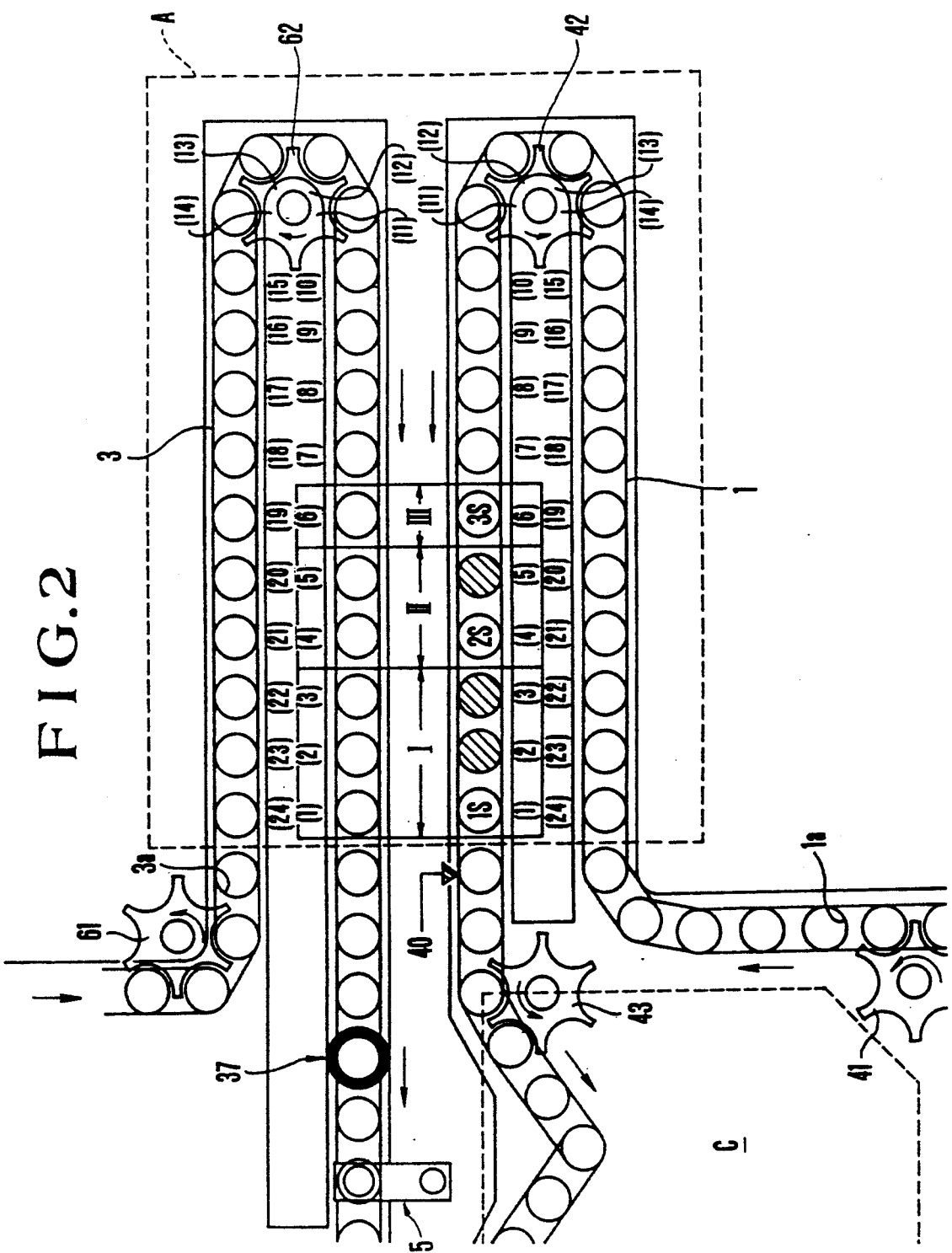
FIG. 2 is an explanatory view useful for explaining in detail the setting work of each container in a set stage A.

FIG. 2 is an explanatory view which is useful for explaining in detail the setting work of each vessel at the set stage A, and FIG. 3 is an explanatory view which is useful for explaining the structure and movement of each vessel 2, 4, which is set at the set stage A, while it is transferred to the suction stage B and to the division-pouring stage D.

In FIG. 2, when the endlessly rotating first conveyor 1 rotates and returns to the set stage A in this embodiment, its openings $1a$, $1a$, $1a$, . . . are empty, and describes a U-shape after turning back at the intermediate point of the transfer path having a predetermined length at the set stage A as shown in the drawing. In the U-shaped transfer path inside this set stage A, the numbers from No. (1) to No. (24) are sequentially put to each opening $1a$ with the position on the upstream side of the transfer path which is close to the suction stage B as the reference point No. (1).

Similarly, when the endlessly rotating second conveyor 3 rotates and returns to the set stage A in this embodiment, its openings $3a$, $3a$, $3a$, . . . are empty, and the transfer path is disposed in the U-shape in the same way as in the first conveyor. The display numbers (1) to (24) are likewise put along the transfer path with the position on the upstream side of transfer close to the division-pouring stage D being the reference point No. (1).

Each vessel is fitted into each opening of these conveyors 1, 3 in the following manner when the first specimen having the three measurement analytes (a, b, c), the second specimen having two measurement analytes (b, c) and the third specimen having one measurement analyte (a) are set, respectively.

The specimen vessel for the first specimen (which is represented as 1S meaning the first specimen, and the specimen vessels for the second and third specimens are likewise represented by 2S, 3S, and so forth) is fitted and set to the opening at the reference point No. (1) of the set stage A of the first conveyor 1. Since this specimen has three measurement analytes, the openings Nos. (2) and (3) are left empty. Incidentally, the empty openings are represented by oblique lines in the drawing for the purpose of simplification.

Next, the specimen vessel 2S is fitted to the opening No. (4) and the opening No. (5) is left empty. The specimen vessel 3S is fitted into the opening No. (6).

In this manner, the open zones I, II and III are defined on the first conveyor 1 depending on the numbers of measurement analytes (3, 2, 1 in this embodiment) as shown in the drawing and each corresponding specimen vessel is fitted into the leading opening of each open zone.

On the other hand, the reaction vessel having the analyte 1, the reaction vessel having the analyte $1b$, the reaction vessel having the analyte $1c$, the reaction vessel having the analyte $2b$, the reaction vessel having the analyte $2c$ and the reaction vessel having the analyte $3a$ are sequentially fitted to the openings Nos. (1), (2), (3), (4), (5) and (6) of the second conveyor 3, respectively and sequentially.

Each reaction vessel is fitted into each opening for each specimen of No. (4) et seq in the same way, whenever necessary.

After the fitting work of the vessels is thus complete, the apparatus is started by pushing an inspection start button not shown in the drawing. In this manner each conveyor is moved and transferred intermittently one opening at a time in the direction represented by the arrow in the drawing. Driving means for causing the intermittent rotation of the conveyors in this embodiment comprises sprockets 41, 42, 43, 61, 62 which are disposed at predetermined positions and are engaged with the conveyors. Since the distance of intermittent rotation of each sprocket is set to be the same, both conveyors are fed in synchronism with each other from the set stage A so that the specimen vessel 2S and the reaction vessel 2b are positioned at the reference point No. (1) when the third intermittent rotation is complete, for example.

In this embodiment, at the position where one specimen vessel is fed out from the set stage A of the first conveyor, the passage of the vessel 2 and the number of subsequent passage of the empty opening are counted by a counter 40. In this case, when the specimen vessel 1S first passes by, the counter 40 counts the passage and counts up by one, and then counts up two empty openings subsequent to the former. In other words, the counter 40 counts three in total for the first specimen. Next, when the passage of the second specimen vessel 2S at this position is detected, the count is updated by confirming the end of the passage of the open zone for the first specimen and at the same time, the next specimen vessel (that is, the specimen vessel 2S) and the number of empty openings till the passage of the next specimen vessel are likewise counted. (In this embodiment, since the number of the empty opening is one in this case, the total number of counts is 2.) The count number detected by this counter 40 is utilized as the data for controlling the stop and holding of the specimen vessels in the suction stage B which will be explained next.

In the suction stage B, the sprocket 44 is disposed in this embodiment in order to accept - stop deliver the specimen vessels 2 in the suction stage B as shown in FIG. 3. This sprocket 44 is controlled in the following manner, for example, by the local microprocessor not shown in the drawing.

The state shown in FIG. 3 represents the case where the first specimen vessel 1S is transferred into the suction stage B. At this time the leading reaction vessel 1a is transferred to and stops at the division-pouring stage D of the second conveyor 3. Under this state, the specimen in the specimen vessel 1S is sucked by the pipet device 8 and dividedly poured into the reaction vessel 1a. In this instance, the specimen in the specimen vessel 1S must also be poured dividedly into the reaction vessels 1b and 1c for the measurement of the remaining two measurement analytes and the rotation of the sprocket 44 is kept stationary for the period necessary for this divided pouring operation so that this specimen vessel 1S is stopped and held at the suction stage B. In the meantime, the reaction vessels 1b and 1c are sequentially transferred into and stopped at the division-pouring stage due to the intermittent driving of the conveyor 3 and the reaction vessel 1c is fed out from the division-pouring stage B during the next intermittent rotation. (This corresponds to the time of transfer of the next reaction vessel 2b into the division-pouring stage D.)

During the period of the stop of rotation of this sprocket 44, too, the intermittent rotation of the first conveyor 1 proceeds at other portions. Therefore, in order to prevent any trouble in the rotation of the conveyor 1 in this case, a stay region C, where the conveyor 1 can stay in the zigzag form, is defined in this embodiment between the sprocket 43 and the sprocket 44. A guide wall 38 having a swell shown in FIG. 3 is provided in this stay region C in such a manner as to define the transfer path of the conveyor 1 lest any problem occurs due to so-called "clogging" of the conveyor.

Next, when specimen suction of the specimen vessel 1S is complete (thrice in total), the next specimen vessel 2S must be transferred into and stopped at the suction stage B for the purpose of the next suction, but two empty openings exist between the first specimen vessel 1S and the next second specimen vessel 2S as shown in FIG. 3. Therefore, if the sprocket 44 is merely rotated intermittently, the empty openings will be naturally stopped and the necessary specimen cannot be poured dividedly into the reaction vessel 2b which is transferred into and stopped at the division-pouring stage. In this case, therefore, the sprocket 44 is rotated continuously for the period corresponding to its stop period so that the next specimen vessel 2S can be transferred to the suction stage B during the next intermittent rotation. Such a control can be made by a predetermined program using the signal from the counter 40 as the data.

After the reaction vessel 3 is fed out from the set stage A by the second conveyor 3, the second reader 37 using a video camera, a bar code reader, or the like, reads the data relating to the predetermined measurement analytes, upstream of the division-pouring stage for this reaction vessel in this embodiment. This read data is used as the data for determining the operation of each mechanism at the reaction-measurement stage E at the post-stage, as described already.

Incidentally, reference numeral 5 in FIG. 3 represents a seal break mechanism and reference numeral 6 represents a diluted solution port.

Figure 4A:
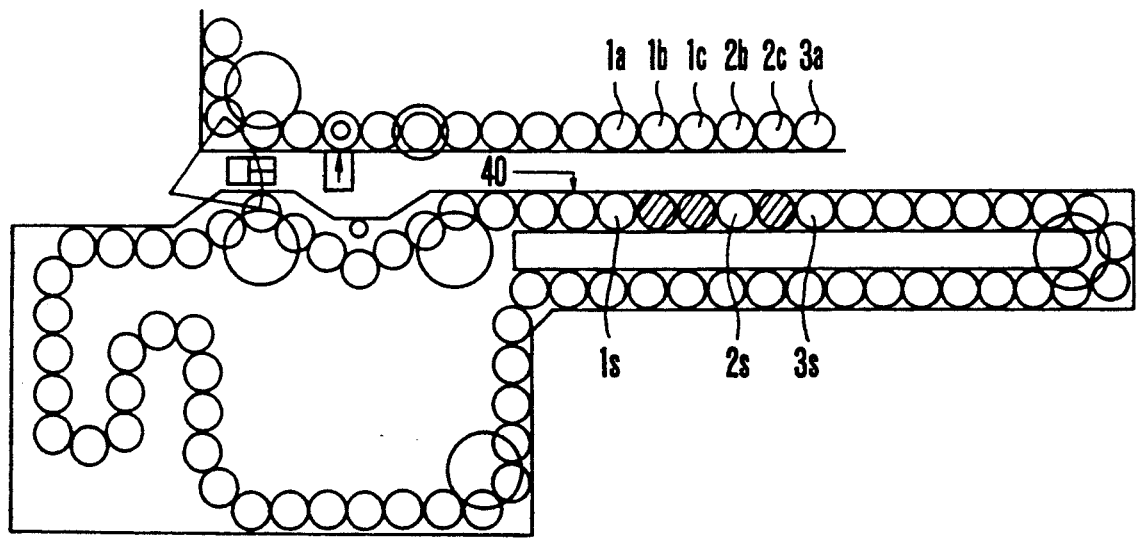
FIGS. 4(a)–4(d) are explanatory views useful for explaining sequentially the movement of each container.
Figure 4B:
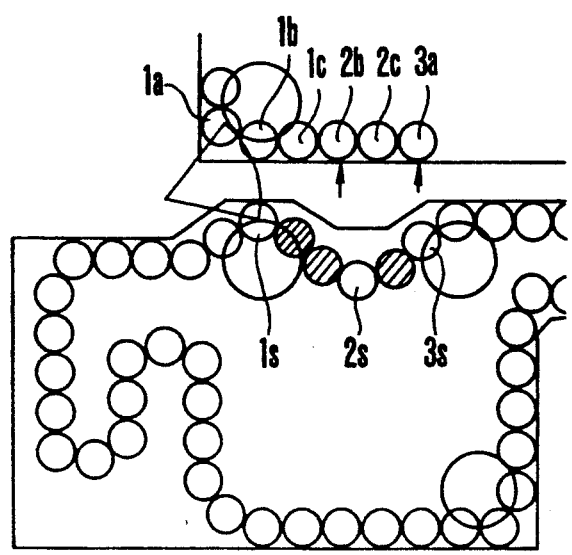
Figure 4C:
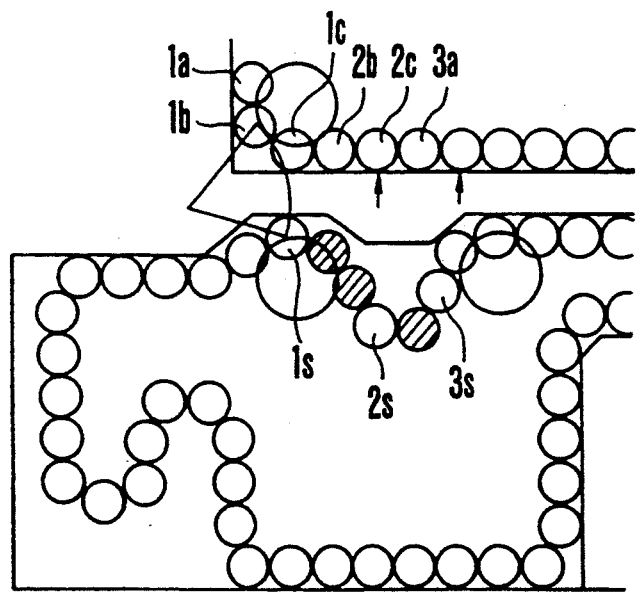
Figure 4D:
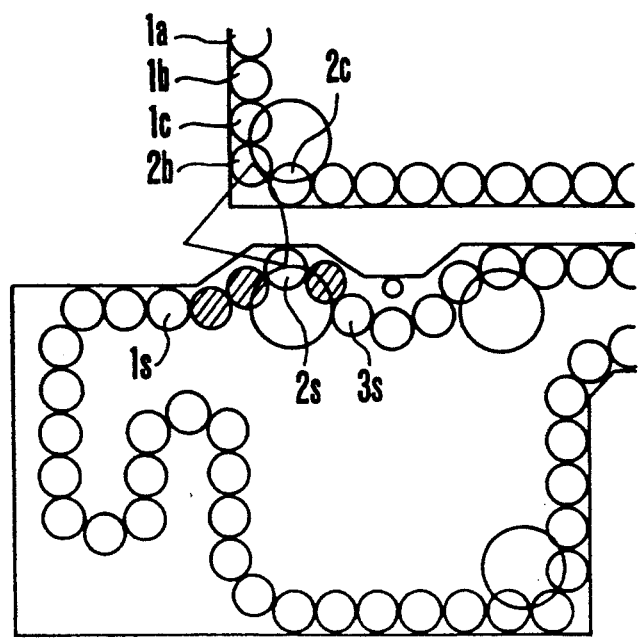

FIGS. 4(a)–4(d) show easily and comprehensively the relation of movement between the specimen vessels and the reaction vessels described above. FIG. 4(a) shows the state where the specimen vessels and the reaction vessels are set to the set stage A, FIGS. 4(b) and 4(c) show that the specimen vessel 1S is stopped at the suction stage B even when the reaction vessels b and c are transferred into and stopped at the division-pouring stage and FIG. 4(d) shows the state where the second specimen vessel 2S is held even when the reaction vessel 2b is transferred into and stopped at the division-pouring stage D.

EMBODIMENT 2:

This embodiment explains the case where 1-step system EIA is carried out. In this case, the reaction vessel into which the fixed antibody fixed to the solid phase and the labeled antibody labeled by an enzyme are charged in advance is used.

As the analyzer to be used in this embodiment, the analyzer explained with reference to FIGS. 1 to 3 can be as such used or the analyzer obtained by omitting the B/F isolation mechanism represented by reference numeral 13 in FIG. 1 can be used, too. In this analyzer, the immunological reaction for forming the composite body comprising the combination of the fixed antibody - the antigen - the labeled antibody proceeds at the division-pouring stage D inside the reaction vessel into which the specimen is poured dividedly, while the reaction vessel is being transferred through the transfer path in the same way as in Embodiment 1. This vessel is transferred to the position of the B/F isolation mechanism represented by reference numeral 25 and the removal of the reaction residue and the like is effected in the same way as in Embodiment 1. Thereafter the amount of the antigen in the specimen is quantitatively determined in the sequence of divided pouring of the substrate and photometry in the same way as in Embodiment 1.

As can be understood from the explanation given above, the fundamental structure of the analyzer of the present invention can be designed in common as both the 1-step system analyzer and the 2-step system analyzer (with the proviso that unnecessary mechanisms are kept stationary or omitted) and can also be constituted as the analyzer capable of selecting both of these systems, whenever necessary.

EMBODIMENT 3

FIG. 5 shows the analyzer in accordance with V still another embodiment of the present invention and is useful for explaining the mechanism for keeping a plurality of reaction vessels stopped and held at the suction stage B after the specimen vessel is transferred onto the suction stage B by the first conveyor 1 for the period of time in which the specimen is dividedly charged into these reaction vessels in the number corresponding to the number of measurement analytes. The characterizing feature of the mechanism of this embodiment resides in that the specimen vessel transferred into the suction stage B is taken down from the first conveyor 1 and on the other hand, unlike Embodiment 1, the intermittent rotation of the first conveyor 1 is kept operated as such at the suction stage, too.

Hereinafter, the characterizing part of this mechanism will be explained. The structure which is analogous to that of Embodiment 1 can be as such used with the exception that the stay for the zigzag stay in the first conveyor 1 need not be disposed, in particular. (However, there is no problem even when such a stay is disposed.)

In the mechanism of this embodiment, a vessel sensor 50 is disposed upstream of the suction stage B (at the opening stop position immediately upstream of the stage B in this embodiment). When this vessel sensor 50 detects the specimen vessel 2, a reciprocating cylinder 51 disposed on the suction stage B is driven in synchronism with the next intermittent rotation of the conveyor 1. This is the characterizing feature of this mechanism.

As can be seen from FIG. 5 showing plane-wise the first conveyor 1 of this embodiment, the conveyor 1 is shown equipped with openings 1a, 1a, 1a, ... on one of the sides of the transfer orbit and each specimen vessel 2 is fitted skippingly into the opening with (n - 1) openings corresponding to the number n of the measurement analytes of each specimen in the same way as in Embodiment 1. (Incidentally, the existence of the vessel is represented by the circle with oblique lines, contrary to the illustration of FIGS. 2 and 3.)

When this specimen vessel 2 is detected by the vessel sensor 50 described above, this detection data is transmitted to a drive control portion, not shown, of the reciprocating cylinder 51 disposed on the suction stage B of the next position and the detected vessel is taken down from the conveyor 1 in synchronism with its transfer into the suction stage B.

The reciprocating cylinder 51 has the following construction. It comprises a plunger 511 capable of moving back and forth while crossing transversely above or below the conveyor from one of the sides of the conveyor to the other in a direction orthogonal to the transferring direction of the conveyor and a return mechanism disposed on the opposite side of the conveyor in such a manner as to face the plunger 511. A semi-circular recess 512 is defined at the advancing tip of the plunger 511 so that the vessel can reliably engage with the tip portion. The return mechanism 513 comprises a pad 514 with which the vessel pushed out sideways from the conveyor from the plunger 511 engages and a return spring 515 which always biases this pad 514 towards the conveyor 1. Accordingly, the pad 514 is normally held at the position shown in FIG. 5(a) at which it is anchored by a stopper not shown in the drawing.

The operation of the reciprocating cylinder 51 having such a structure is as follows. First of all, the plunger 511 moves upward in the drawing from the state shown in FIG. 5(a) in response to the signal transmission from the vessel sensor 50 and the transfer operation of the vessel to the suction stage B by the rotation of the conveyor. Accordingly, the recess 512 at the tip of the plunger 511 engages with the vessel which is fitted into the opening represented by the order 3 in the drawing and as the plunger 511 moves forward further, the vessel is pushed sideways of the conveyor (see FIG. 5(b)).

Specimen suction is made by the pipet device, not shown, from the specimen vessel taken down from the conveyor under this state. On the other hand, since the conveyor 1 in this embodiment keeps the predetermined intermittent rotation as described above, the opening (empty) represented by the order 4 in the drawing is transferred into the stage B while the opening at the position represented by the order 5 is transferred to the position of the vessel sensor 50.

Here, the reciprocating cylinder 51 returns to the initial position or in other words, the plunger 511 moves back (see FIG. 5(c)). In this case, the vessel taken down from the conveyor moves and returns to the conveyor 1 side by the spring force of the return spring 515 and since the opening of the order 4 is empty in this case, the vessel returns again to the state where it is transferred by the conveyor.

Next, when the conveyor makes a next intermittent rotation, the opening of the order 5 is conveyed into the suction stage B (see FIG. 5(d)) and this specimen vessel is taken down from the conveyor in the same way as described above and the conveyor makes consecutively the next intermittent operation (see FIG. 5(e)).

As described above, in the apparatus of this embodiment, the intermittent rotation of the conveyor can be made at the suction stage, too, without any difference from other portions. Accordingly, drive control of the conveyor can be designed more simply.

Incidentally, the vessels taken down from the conveyor at the suction stage B are used vessels by virtue of the suction of the specimen therein. For this reason, they may be discharged outside the analyzer by another discard means without returning them again back to the conveyor.

As described above, the analyzer of the present invention can easily cope with a large number of specimens having different measurement analytes, can measure them easily and rapidly, and has an excellent structure suitable for random access. Moreover, the analyzer of the invention provides another advantage in that the addition of specimens can be made easily after the measurement operation by the analyzer is started.

The analyzer of the present invention provides the effect that the manual work necessary for the measurement can be completed by merely putting the specimen vessels into which the specimens are charged and the reaction vessels having different contents for the measurement analytes for the immunological reaction on the conveyor, and makes the operation extremely easy with reduced mistakes operation.

Furthermore, the analyzer of the present invention has high design freedom such that the analyzer can cope with an analyzer for a relatively small number of specimens to be processed and for a large number of specimens while keeping in common the fundamental structure of the analyzer, by merely changing the length of the conveyor.

What is claimed is:

1. An automatic immunoassay analyzer, comprising:
   an endless specimen vessel transfer conveyor having a plurality of support portions for supporting a plurality of specimen vessels, said specimen vessel transfer conveyor conveying said plurality of support portions in a first direction;
   a reaction vessel transfer conveyor having a plurality of support portions for supporting a plurality of reaction vessels, said reaction vessel transfer conveyor conveying said plurality of support portions in said first direction;
   division-pouring means for sucking a specimen from a specimen vessel stopped at a suction stage and pouring a portion thereof into a reaction vessel stopped at a division-pouring stage, said specimen vessel transfer conveyor including an endless transport path thereof from a first set stage at which said specimen vessels fitted into and supported by said support portions, and returning to said first set stage through said suction stage at which said specimen inside each of said specimen vessels being sucked by said division-pouring means;
   first conveyor driving means for sequentially conveying and stopping said specimen vessels to and at said suction stage corresponding to a respective support portion zone determined sequentially by zoning said support portions of said specimen vessel transfer conveyor by a number corresponding to a number of measurement analytes of each of said specimens supported;
   said reaction vessel transfer conveyor including a second endless transport path thereof from a second set stage at which said reaction vessels fitted into and supported by said support portions, through said division-pouring stage at which a portion of the specimen sucked from a respective specimen vessel being poured into said reaction vessel by said division-pouring means, through a reaction-measurement stage at which a measurement of an immunological reaction inside said reaction vessels being performed, and returning to said second set stage;
   second conveyor driving means for sequentially transferring, stopping and feeding out said reaction vessels to, at and from said division-pouring stage when said reaction vessels corresponding to measurement analytes of each of said specimen being sequentially supported by said support portions of said reaction vessel transfer conveyor; and
   means for synchronously and simultaneously actuating said first and second conveyor driving means;
   holding means downstream of said first conveyor driving means for stopping and holding one of said specimen vessels transferred into said suction stage for a predetermined time period independent of said first conveyor driving means in which said reaction vessels corresponding to said specimen being transferred and stopped sequentially into and at said division-pouring stage,
   means for accommodating excess specimen vessel transfer conveyor and specimen vessels between said holding means and said first conveyor driving means as a result of any difference in said time period and said actuation of said first conveyor driving means.

2. An automatic immunoassay analyzer according to claim 1, wherein at least one of said specimen vessel transfer conveyor and said reaction vessel transfer conveyor is a conveyor capable of zigzag movement inside a horizontal plane.

3. An automatic immunoassay analyzer according to claim 2, wherein said conveyor capable of zigzag movement is an endless chain conveyor.

4. An automatic immunoassay analyzer according to claim 2, wherein at least one of said first conveyor driving means and said second conveyor driving means for rotating the respective one of said specimen vessel transfer conveyor and said reaction vessel transfer conveyor capable of zigzag movement is a sprocket rotating intermittently while engaging the respective conveyor.

5. An automatic immunoassay analyzer according to claim 4, wherein said sprockets of said first and second conveyor driving means rotate synchronously.

6. An automatic immunoassay analyzer according to claim 2, wherein said first conveyor driving means for rotating said specimen vessel transfer conveyor comprises a first sprocket disposed at said suction stage for transferring, stopping and feeding out said specimen vessel into, at and from said suction stage and a plurality of second sprockets for feeding intermittently said support portions one frame at a time, disposed at positions other than at said suction stage.

7. An automatic immunoassay analyzer according to claim 6, further comprising first and second stay regions, said first and second stay regions each comprising an area at which said specimen vessel transfer conveyor fed one frame at a time by said plurality of second sprockets remains in a zig-zag form, said first and second stay regions being disposed upstream and downstream of said suction stage, respectively.

8. An automatic immunoassay analyzer according to claim 7, wherein said holding means stops said first sprocket for a stop period corresponding to a number of measurement analytes of each of said specimens, and rotates continuously said first sprocket at a same timing as a next one-frame feed operation of said plurality of second sprockets after said stop period until a next one of said specimen vessels on said conveyor staying in the zig-zag form of said first stay region being transferred into said suction stage.

9. An automatic immunoassay analyzer according to claim 1, wherein said holding means moves said specimen vessels transferred to said suction stage from said specimen vessel transfer conveyor in a predetermined direction, said predetermined direction being transverse to said first direction of said specimen vessel transfer conveyor.

10. An automatic immunoassay analyzer according to claim 8, further comprising counter means for detecting the number of measurement analytes of each of said specimen vessels being transferred by said specimen vessel transfer conveyor, said counter means being disposed at a position upstream of said suction stage of said specimen vessel transfer conveyor, and control means for driving and controlling said first sprocket to advance said conveyor a predetermined distance based on the number of measurement analytes detected by said counter means.

11. An automatic immunoassay analyzer according to claim 10, wherein said counter means includes means for detecting said specimen vessel supported by a leading one of said support portions of each of said support portion zones, and means for detecting the number of the measurement analytes by counting empty support portions not supporting thereon subsequent specimen vessels.

12. An automatic immunoassay analyzer according to claim 1, wherein said support portions of both of said specimen vessel transfer conveyor and said reaction vessel transfer conveyor are disposed equidistantly in said first direction.

13. An automatic immunoassay analyzer according to claim 1, wherein said first transport path of said specimen vessel transfer conveyor in said first set stage and said second transport path of said reaction vessel transfer conveyor in said second set stage are disposed in parallel with each other.

14. An automatic immunoassay analyzer according to claim 1, further comprising first read means for reading a mark specifying said specimen displayed on said specimen vessel disposed at a position upstream of said suction stage of said specimen vessel transfer conveyor in said first direction.

15. An automatic immunoassay analyzer according to claim 1 further comprising second read means for reading measurement analytes displayed on said reaction vessel disposed at a position upstream of said division-pouring stage of said reaction vessel transfer conveyor.

16. An automatic immunoassay analyzer according to claim 1, wherein said division-pouring means comprises a pipet device moving between said suction stage of said specimen vessel transfer conveyor and said division-pouring stage of said reaction vessel transfer conveyor.

17. An automatic immunoassay analyzer according to claim 1, wherein an antibody causing the immunological reaction with an antigen contained in said specimen is prepacked into said reaction vessel.

18. An automatic immunoassay analyzer according to claim 17, wherein the antibody is fixed to a solid phase.

19. An automatic immunoassay analyzer according to claim 1, wherein said reaction-measurement stage to which said reaction vessel conveyed comprises reagent division-pouring means for charging a portion of a reagent containing an antibody causing the immunological reaction with an antigen contained in said specimen, into said reaction vessel.

20. An automatic immunoassay analyzer according to claim 19, wherein said antibody contained in said reagent being labeled with an enzyme, and said reaction-measurement stage includes substrate division-pouring means for charging a portion of a substrate into said reaction vessel causing an optically detectable change by activity of said enzyme and optical detection means for detecting a change in said substrate as a result of said immunological reaction.

21. An automatic immunoassay analyzer according to claim 20, further comprising recording means for recording the detection result by said optical detection means.

22. An automatic immunoassay analyzer according to claim 21, further comprising first read means for reading a mark specifying said specimen which is displayed on said specimen vessel disposed at a position upstream of said suction stage of said specimen vessel transfer conveyor in said first direction, and
second read means for reading the measurement analytes displayed on said reaction vessel disposed at a position upstream of said division-pouring stage of said reaction vessel transfer conveyor,
wherein said recording means records a read result of said first read means and a read result of said second read means with a measurement result of said optical detection means.

23. An automatic immunoassay analyzer according to claim 1, further comprising a solid having magnetic susceptibility prepacked into said reaction vessel, and means for imparting an oscillating magnetic field on said reaction vessel disposed on said reaction-measurement stage.

24. An automatic immunoassay analyzer according to claim 18, further comprising a solid having magnetic susceptibility pre-packed into said reaction vessel, and means for imparting an oscillating magnetic field on said reaction vessel disposed on said reaction-measurement stage,
wherein said solid pre-packed into said reaction vessel comprises said solid phase.

25. An automatic immunoassay analyzer according to claim 1, wherein support portion zones being sequentially zoned on said specimen vessel transfer conveyor by the number of measurement analytes of said specimen, and a corresponding one of said specimen vessels being supported by a leading support portion of each of said support portion zones.

26. An automatic immunoassay analyzer according to claim 19, further comprising means for incubating said reaction vessel containing said reagent and said specimen and being positioned at said reaction-measurement stage to which said reaction vessel being transferred, said incubating means comprising a heat generator bonded to a lower surface of a sheet forming said second transport path, wherein current flowing through said heat generator to control the temperature of said reaction-measurement stage to a predetermined temperature.

27. An automatic immunoassay analyzer according to claim 8, further comprising a vessel sensor disposed upstream of said suction stage for detecting a specimen vessel, and a reciprocating cylinder disposed on said suction stage,
wherein upon detection of one of said specimen vessels, said reciprocating cylinder being driven in synchronism with the next intermittent rotation of the said specimen vessel transfer conveyor,
said reciprocating cylinder including a plunger movable in first and second directions opposite to one another across said specimen vessel transfer conveyor from a first side thereof to a second side thereof in a direction orthogonal to said first direction of said specimen vessel transfer conveyor, and a return mechanism disposed on said second side of said specimen vessel transfer conveyor to oppose said plunger,
wherein said plunger being engageable with said specimen vessel detected by said vessel sensor to push the specimen vessel outwardly from said specimen vessel transfer conveyor, and said return mechanism comprises a pad and a return spring for biasing said pad towards said specimen vessel transfer conveyor.

* * * * *